US010335545B2

(12) United States Patent
Cabiri (10) Patent No.: US 10,335,545 B2
(45) Date of Patent: Jul. 2, 2019

(54) TIME DEPENDENT DRUG DELIVERY APPARATUS (75) Inventor: Oz Cabiri, Macabim-Reut (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 0 days.

(21) Appl. No.: 14/372,384

(22) PCT Filed: Aug. 14, 2012

(86) PCT No.: PCT/US2012/050696
§ 371 (c)(1),
(2), (4) Date: Jul. 15, 2014

(87) PCT Pub. No.: WO2013/115843
PCT Pub. Date: Aug. 8, 2013

(65) Prior Publication Data
US 2015/0011965 A1    Jan. 8, 2015

Related U.S. Application Data (60) Provisional application No. 61/592,978, filed on Jan. 31, 2012.

(51) Int. Cl.
*A61M 5/172* (2006.01)
*A61M 5/142* (2006.01)
(Continued)

(52) U.S. Cl.
CPC ........ *A61M 5/172* (2013.01); *A61M 5/14244* (2013.01); *A61M 5/14248* (2013.01);
(Continued)

(58) Field of Classification Search
CPC .............. A61M 5/172; A61M 5/14248; A61M 5/14244; A61M 39/0247;
(Continued)

(56) References Cited

U.S. PATENT DOCUMENTS 3,946,732 A   3/1976   Hurscham
3,994,295 A   11/1976  Wulff
(Continued)

FOREIGN PATENT DOCUMENTS

CN   101868273 A   10/2010
CN   102022308 A   4/2011
(Continued)

OTHER PUBLICATIONS

Int'l Search Report and Written Opinion dated Jun. 30, 2014 in Int'l Application No. PCT/US2013/031598.
(Continued)

*Primary Examiner* — Jenna Zhang
(74) *Attorney, Agent, or Firm* — Panitch Schwarze Belisario & Nadel LLP (57) ABSTRACT

A drug delivery apparatus provides autonomous variable rate delivery of a substance. In some embodiments, the delivery apparatus may be programmable. In some embodiments, the delivery apparatus may be disposable. Optionally the rate of delivery may be dependent on a temperature of a component of the apparatus. Optionally, there may be a time delay between activation of the apparatus and delivery power of the substance.

20 Claims, 5 Drawing Sheets

(51) Int. Cl.
*G06F 19/00* (2018.01)
*A61M 5/44* (2006.01)
*G16H 40/60* (2018.01)
*G16H 40/67* (2018.01)

(52) U.S. Cl.
CPC .......... *A61M 5/44* (2013.01); *G06F 19/3418* (2013.01); *G16H 40/60* (2018.01); *G16H 40/67* (2018.01); *A61M 2205/276* (2013.01); *A61M 2205/3306* (2013.01); *A61M 2205/3368* (2013.01); *A61M 2205/36* (2013.01); *A61M 2205/3613* (2013.01); *A61M 2205/50* (2013.01); *A61M 2205/52* (2013.01); *A61M 2205/702* (2013.01); *A61M 2205/8212* (2013.01); *A61M 2230/50* (2013.01)

(58) Field of Classification Search
CPC .... A61M 2205/3613; A61M 2205/276; A61M 2205/36; A61M 2205/583; A61M 2205/584; A61M 2005/3125; A61M 2005/3126; A61M 2205/3368; A61M 2205/5841; A61M 5/44; A61M 2230/50; A61M 2205/702; A61M 2205/50; A61M 2205/3306; A61M 2205/8212; A61M 2205/52; A61J 2200/72; G16H 40/60; G16H 40/67; G06F 19/3418
See application file for complete search history.

(56) References Cited

U.S. PATENT DOCUMENTS

| | | | |
|---|---|---|---|
| 4,167,663 A * | 9/1979 | Granzow, Jr. | A61M 5/44 219/497 |
| 4,273,122 A | 6/1981 | Whitney et al. | |
| 4,396,385 A | 8/1983 | Kelly et al. | |
| 4,601,702 A | 7/1986 | Hudson | |
| 4,634,426 A * | 1/1987 | Kamen | A61M 5/1689 128/DIG. 13 |
| 4,886,499 A | 12/1989 | Cirelli et al. | |
| 4,908,014 A * | 3/1990 | Kroyer | A61M 1/369 128/DIG. 3 |
| 4,919,596 A | 4/1990 | Slate et al. | |
| 4,950,235 A | 8/1990 | Slate et al. | |
| 4,950,246 A | 8/1990 | Muller | |
| 5,109,850 A | 5/1992 | Blanco et al. | |
| 5,131,816 A * | 7/1992 | Brown | A61M 5/142 128/DIG. 12 |
| 5,254,096 A | 10/1993 | Rondelet et al. | |
| 5,342,313 A | 8/1994 | Campbell et al. | |
| 5,354,287 A | 10/1994 | Wacks | |
| 5,383,865 A | 1/1995 | Michel | |
| 5,411,482 A * | 5/1995 | Campbell | A61M 5/148 604/153 |
| 5,501,665 A | 3/1996 | Jhuboo et al. | |
| 5,593,390 A | 1/1997 | Castellano et al. | |
| 5,616,132 A | 4/1997 | Newman | |
| 5,643,218 A | 7/1997 | Lynn et al. | |
| 5,647,853 A | 7/1997 | Feldmann et al. | |
| 5,658,133 A | 8/1997 | Anderson et al. | |
| 5,690,618 A | 11/1997 | Smith et al. | |
| D393,314 S | 4/1998 | Meisner et al. | |
| 5,800,420 A | 9/1998 | Gross et al. | |
| 5,807,375 A | 9/1998 | Gross et al. | |
| 5,814,020 A * | 9/1998 | Gross | A61M 5/14248 604/141 |
| 5,851,197 A | 12/1998 | Marano et al. | |
| 5,858,001 A | 1/1999 | Tsals et al. | |
| 5,858,008 A | 1/1999 | Capaccio | |
| 5,931,814 A | 8/1999 | Alex et al. | |
| 5,957,895 A | 9/1999 | Sage et al. | |
| 5,993,423 A | 11/1999 | Choi | |
| 5,997,501 A | 12/1999 | Gross et al. | |
| 6,004,297 A | 12/1999 | Steenfeldt-Jensen et al. | |
| 6,064,797 A | 5/2000 | Crittendon et al. | |
| 6,074,369 A | 6/2000 | Sage et al. | |
| 6,175,688 B1 * | 1/2001 | Cassidy | A61M 5/365 392/470 |
| 6,186,982 B1 | 2/2001 | Gross et al. | |
| 6,200,289 B1 | 3/2001 | Hochman et al. | |
| 6,248,093 B1 | 6/2001 | Moberg | |
| 6,277,095 B1 | 8/2001 | Kriesel et al. | |
| 6,277,098 B1 | 8/2001 | Klitmose et al. | |
| 6,277,099 B1 | 8/2001 | Strowe et al. | |
| 6,287,283 B1 | 9/2001 | Ljunggreen et al. | |
| 6,362,591 B1 | 3/2002 | Moberg | |
| 6,391,005 B1 | 5/2002 | Lum et al. | |
| 6,423,029 B1 | 7/2002 | Elsberry | |
| 6,423,035 B1 * | 7/2002 | Das | A61M 5/1456 128/DIG. 1 |
| D465,026 S | 10/2002 | May et al. | |
| 6,458,102 B1 | 10/2002 | Mann et al. | |
| 6,485,461 B1 | 11/2002 | Mason et al. | |
| 6,485,465 B2 | 11/2002 | Moberg et al. | |
| 6,500,150 B1 | 12/2002 | Gross et al. | |
| 6,517,517 B1 | 2/2003 | Farrugia et al. | |
| D471,274 S | 3/2003 | Diaz et al. | |
| D471,983 S | 3/2003 | Hippolyte et al. | |
| 6,530,901 B1 | 3/2003 | Tsukada et al. | |
| 6,555,986 B2 | 4/2003 | Moberg | |
| 6,558,351 B1 | 5/2003 | Steil et al. | |
| 6,589,229 B1 | 7/2003 | Connelly et al. | |
| 6,595,956 B1 | 7/2003 | Gross et al. | |
| 6,595,960 B2 | 7/2003 | West et al. | |
| 6,645,181 B1 | 11/2003 | Lavi et al. | |
| 6,652,482 B2 | 11/2003 | Hochman | |
| 6,656,158 B2 | 12/2003 | Mahoney et al. | |
| 6,656,159 B2 | 12/2003 | Flaherty | |
| 6,659,980 B2 | 12/2003 | Moberg et al. | |
| 6,673,033 B1 | 1/2004 | Sciulli et al. | |
| 6,679,862 B2 | 1/2004 | Diaz et al. | |
| 6,699,218 B2 | 3/2004 | Flaherty et al. | |
| 6,749,587 B2 | 6/2004 | Flaherty | |
| 6,768,425 B2 | 7/2004 | Flaherty et al. | |
| 6,786,890 B2 | 9/2004 | Preuthun et al. | |
| 6,800,071 B1 | 10/2004 | McConnell et al. | |
| 6,805,687 B2 | 10/2004 | Dextradeur et al. | |
| 6,824,529 B2 | 11/2004 | Gross et al. | |
| 6,830,558 B2 | 12/2004 | Flaherty et al. | |
| 6,843,782 B2 | 1/2005 | Gross et al. | |
| 6,854,620 B2 | 2/2005 | Ramey | |
| 6,905,298 B1 | 6/2005 | Haring | |
| 6,908,452 B2 | 6/2005 | Diaz et al. | |
| 6,933,693 B2 | 8/2005 | Schuchmann | |
| 6,950,028 B2 * | 9/2005 | Zweig | G01K 3/04 340/584 |
| 6,960,192 B1 * | 11/2005 | Flaherty | A61M 5/14248 604/131 |
| 7,001,360 B2 | 2/2006 | Veasey et al. | |
| 7,048,715 B2 | 5/2006 | Diaz et al. | |
| 7,060,059 B2 | 6/2006 | Keith et al. | |
| 7,122,982 B2 | 10/2006 | Sasaya et al. | |
| 7,128,727 B2 | 10/2006 | Flaherty et al. | |
| 7,144,384 B2 | 12/2006 | Gorman et al. | |
| 7,193,521 B2 | 3/2007 | Moberg et al. | |
| D544,092 S | 6/2007 | Lewis | |
| 7,247,149 B2 | 7/2007 | Beyerlein | |
| 7,250,037 B2 | 7/2007 | Shermer et al. | |
| 7,267,669 B2 | 9/2007 | Staunton et al. | |
| 7,303,549 B2 | 12/2007 | Flaherty et al. | |
| 7,390,314 B2 | 6/2008 | Stutz, Jr. et al. | |
| 7,407,493 B2 | 8/2008 | Cane' | |
| 7,455,663 B2 | 11/2008 | Bikovsky | |
| 7,459,571 B2 | 12/2008 | Schlitter et al. | |
| 7,465,290 B2 | 12/2008 | Reilly | |
| 7,497,842 B2 | 3/2009 | Diaz et al. | |
| 7,524,304 B2 | 4/2009 | Genosar | |
| 7,530,964 B2 | 5/2009 | Lavi et al. | |
| 7,547,281 B2 | 6/2009 | Hayes et al. | |
| 7,563,253 B2 | 7/2009 | Tanner et al. | |
| 7,565,208 B2 | 7/2009 | Harris et al. | |
| 7,569,050 B2 | 8/2009 | Moberg et al. | |
| D600,341 S | 9/2009 | Loerwald | |

(56) References Cited

U.S. PATENT DOCUMENTS

| | | |
|---|---|---|
| 7,585,287 B2 | 9/2009 | Bresina et al. |
| 7,588,559 B2 | 9/2009 | Aravena et al. |
| D602,155 S | 10/2009 | Foley et al. |
| D602,586 S | 10/2009 | Foley et al. |
| D604,835 S | 11/2009 | Conley |
| 7,621,893 B2 | 11/2009 | Moberg et al. |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,692,399 B2 | 4/2010 | Harriman et al. |
| 7,699,829 B2 | 4/2010 | Harris et al. |
| 7,699,833 B2 | 4/2010 | Moberg et al. |
| 7,704,227 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,753,879 B2 | 7/2010 | Mernoe |
| 7,766,873 B2 | 8/2010 | Moberg et al. |
| 7,776,030 B2 | 8/2010 | Estes et al. |
| 7,780,636 B2 | 8/2010 | Radmer et al. |
| 7,780,637 B2 | 8/2010 | Jerde et al. |
| 7,789,857 B2 | 9/2010 | Moberg et al. |
| 7,789,862 B2 | 9/2010 | Thorne, Jr. |
| 7,801,599 B2 | 9/2010 | Young et al. |
| 7,806,868 B2 | 10/2010 | De Polo et al. |
| 7,815,622 B2 | 10/2010 | Istoc et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,857,131 B2 | 12/2010 | Vedrine |
| 7,879,025 B2 | 2/2011 | Jacobson et al. |
| 7,879,026 B2 | 2/2011 | Estes et al. |
| 7,892,206 B2 | 2/2011 | Moberg et al. |
| 7,918,825 B2 | 4/2011 | O'Connor et al. |
| 7,918,843 B2 | 4/2011 | Genosar et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,436 B2 | 11/2011 | Causey et al. |
| 8,062,253 B2 | 11/2011 | Nielsen et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,923 B2 | 4/2012 | Adams et al. |
| 8,167,841 B2 | 5/2012 | Teisen-Simony et al. |
| 8,172,804 B2 | 5/2012 | Bikovsky |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,267,893 B2 | 9/2012 | Moberg et al. |
| 8,267,921 B2 | 9/2012 | Yodfat et al. |
| 8,287,520 B2 | 10/2012 | Drew et al. |
| 8,308,679 B2 | 11/2012 | Hanson et al. |
| 8,348,898 B2 | 1/2013 | Cabiri |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,495,918 B2 | 7/2013 | Bazargan et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,574,216 B2 | 11/2013 | Istoc et al. |
| 8,603,026 B2 | 12/2013 | Favreau |
| 8,603,027 B2 | 12/2013 | Favreau |
| 8,617,110 B2 | 12/2013 | Moberg et al. |
| 8,628,510 B2 | 1/2014 | Bazargan et al. |
| 8,647,074 B2 | 2/2014 | Moberg et al. |
| 8,647,296 B2 | 2/2014 | Moberg et al. |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,810,394 B2 | 8/2014 | Kalpin |
| 9,463,280 B2 | 10/2016 | Cabiri |
| 2002/0040208 A1 | 4/2002 | Flaherty et al. |
| 2002/0043951 A1 | 4/2002 | Moberg |
| 2002/0055711 A1 | 5/2002 | Lavi et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0199825 A1 | 10/2003 | Flaherty |
| 2004/0085215 A1 | 5/2004 | Moberg et al. |
| 2004/0092873 A1 | 5/2004 | Moberg |
| 2004/0116866 A1 | 6/2004 | Gorman et al. |
| 2004/0260233 A1 | 12/2004 | Garibotto et al. |
| 2005/0065472 A1 | 3/2005 | Cindrich et al. |
| 2005/0070845 A1* | 3/2005 | Faries, Jr. ............ A61M 5/148 604/98.01 |
| 2005/0071487 A1 | 3/2005 | Lu et al. |
| 2005/0171512 A1 | 8/2005 | Flaherty |
| 2005/0177136 A1 | 8/2005 | Miller |

(56) References Cited

U.S. PATENT DOCUMENTS

| | | |
|---|---|---|
| 2005/0197650 A1 | 9/2005 | Sugimoto et al. |
| 2005/0238507 A1 | 10/2005 | Dilanni et al. |
| 2005/0258714 A1 | 11/2005 | Henderson et al. |
| 2006/0095014 A1 | 5/2006 | Ethelfeld |
| 2006/0122577 A1* | 6/2006 | Poulsen .............. A61M 5/1413 604/890.1 |
| 2006/0173408 A1 | 8/2006 | Wyrick |
| 2006/0173439 A1 | 8/2006 | Thorne et al. |
| 2006/0184154 A1 | 8/2006 | Moberg et al. |
| 2006/0229569 A1 | 10/2006 | Lavi et al. |
| 2006/0264890 A1 | 11/2006 | Moberg et al. |
| 2006/0283465 A1 | 12/2006 | Nickel et al. |
| 2007/0021733 A1 | 1/2007 | Hansen et al. |
| 2007/0049865 A1 | 3/2007 | Radmer et al. |
| 2007/0118405 A1 | 5/2007 | Campbell et al. |
| 2007/0149926 A1 | 6/2007 | Moberg et al. |
| 2007/0167912 A1* | 7/2007 | Causey .............. A61M 5/14244 604/131 |
| 2007/0191770 A1 | 8/2007 | Moberg et al. |
| 2007/0219480 A1* | 9/2007 | Kamen ................ G05D 7/0647 604/20 |
| 2007/0282269 A1 | 12/2007 | Carter et al. |
| 2008/0033369 A1 | 2/2008 | Kohlbrenner et al. |
| 2008/0051710 A1 | 2/2008 | Moberg et al. |
| 2008/0051711 A1 | 2/2008 | Mounce et al. |
| 2008/0051727 A1 | 2/2008 | Moberg et al. |
| 2008/0059133 A1 | 3/2008 | Edwards et al. |
| 2008/0125700 A1* | 5/2008 | Moberg ............ A61M 5/14244 604/67 |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0215006 A1 | 9/2008 | Thorkild |
| 2008/0221522 A1 | 9/2008 | Moberg et al. |
| 2008/0221523 A1 | 9/2008 | Moberg et al. |
| 2008/0269723 A1 | 10/2008 | Mastrototaro et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0054750 A1 | 2/2009 | Jennewine |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0124977 A1 | 5/2009 | Jensen |
| 2009/0149830 A1 | 6/2009 | Spector |
| 2009/0182277 A1 | 7/2009 | Carter |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0299397 A1 | 12/2009 | Ruan et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0037680 A1 | 2/2010 | Moberg et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0145303 A1 | 6/2010 | Yodfat et al. |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0217192 A1 | 8/2010 | Moberg et al. |
| 2010/0217193 A1 | 8/2010 | Moberg et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0276411 A1* | 11/2010 | Hansen .................. A61M 5/44 219/385 |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0060284 A1* | 3/2011 | Harr .................. A61M 5/14244 604/153 |
| 2011/0119033 A1 | 5/2011 | Moberg et al. |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0178472 A1 | 7/2011 | Cabiri |
| 2011/0184342 A1 | 7/2011 | Pesach et al. |
| 2011/0201998 A1 | 8/2011 | Pongpairochana et al. |
| 2011/0224614 A1 | 9/2011 | Moberg et al. |
| 2011/0233393 A1 | 9/2011 | Hanson et al. |
| 2011/0238031 A1 | 9/2011 | Adair et al. |
| 2011/0245773 A1 | 10/2011 | Estes et al. |
| 2011/0264383 A1 | 10/2011 | Moberg et al. |
| 2011/0270160 A1 | 11/2011 | Mernoe |
| 2011/0282282 A1 | 11/2011 | Lorenzen et al. |
| 2011/0295205 A1 | 12/2011 | Kaufmann et al. |
| 2011/0313238 A1 | 12/2011 | Reichenbach et al. |
| 2011/0313351 A1* | 12/2011 | Kamen ............ A61M 5/14244 604/67 |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022499 A1 | 1/2012 | Anderson et al. |
| 2012/0025995 A1 | 2/2012 | Moberg et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041370 A1 | 2/2012 | Moberg et al. |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete, Jr. et al. |
| 2012/0296174 A1* | 11/2012 | McCombie ........ A61B 5/02427 600/301 |
| 2012/0310153 A1 | 12/2012 | Moberg et al. |
| 2013/0068319 A1 | 3/2013 | Plumptre et al. |
| 2013/0096509 A1 | 4/2013 | Avery et al. |
| 2013/0133438 A1 | 5/2013 | Kow et al. |
| 2013/0175192 A1 | 7/2013 | Iio et al. |
| 2013/0218089 A1 | 8/2013 | Davies et al. |
| 2013/0218092 A1 | 8/2013 | Davies et al. |
| 2013/0237953 A1 | 9/2013 | Kow et al. |
| 2013/0245595 A1 | 9/2013 | Kow et al. |
| 2013/0253419 A1 | 9/2013 | Favreau |
| 2013/0253420 A1 | 9/2013 | Favreau |
| 2013/0253421 A1 | 9/2013 | Favreau |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |

(56) References Cited

U.S. PATENT DOCUMENTS

| | | |
|---|---|---|
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0171881 A1 | 6/2014 | Cabiri |
| 2014/0194819 A1 | 7/2014 | Maule et al. |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0210631 A1 | 7/2014 | Zavis |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |
| 2014/0288511 A1 | 9/2014 | Tan-Malecki et al. |
| 2015/0011976 A1 | 1/2015 | Vouillamoz et al. |
| 2016/0015910 A1 | 1/2016 | Mukai et al. |

FOREIGN PATENT DOCUMENTS

| | | |
|---|---|---|
| EP | 0401179 A1 | 12/1990 |
| EP | 1666080 A1 | 6/2006 |
| EP | 2060606 A1 | 5/2009 |
| EP | 2345441 A1 | 7/2011 |
| EP | 2454483 B1 | 8/2015 |
| WO | 8911302 A1 | 11/1989 |
| WO | 9009202 A1 | 8/1990 |
| WO | 9521645 A1 | 8/1995 |
| WO | 9632975 A1 | 10/1996 |
| WO | 9721457 A1 | 6/1997 |
| WO | 9733638 A1 | 9/1997 |
| WO | 2007092618 A2 | 8/2007 |
| WO | 2007130868 A1 | 11/2007 |
| WO | 2008024810 A2 | 2/2008 |
| WO | 2008024814 A2 | 2/2008 |
| WO | 2008129549 A1 | 10/2008 |
| WO | 2009081262 A1 | 7/2009 |
| WO | 2011090955 A1 | 7/2011 |
| WO | 2011113806 A1 | 9/2011 |
| WO | 2012032411 A2 | 3/2012 |
| WO | 2014081411 A1 | 5/2014 |

OTHER PUBLICATIONS

Int'l Search Report and Written Opinion dated Aug. 28, 2014 in Int'l Application No. PCT/US2014/035662.
Int'l Preliminary Report on Patentability dated Aug. 14, 2014 in Int'l Application No. PCT/US2012/050696.
U.S. Appl. No. 13/429,942 by Cabiri, filed Mar. 26, 2012.
U.S. Appl. No. 13/886,867 by Cabiri, filed May 3, 2013.
Int'l Search Report and Written Opinion dated Apr. 5, 2013 in Int'l Application No. PCT/US2012/050696.
Office Action dated Aug. 15, 2013 in U.S. Appl. No. 13/429,942 by Cabiri.
Office Action dated Jan. 16, 2014 in U.S. Appl. No. 13/429,942 by Cabiri.
Office Action dated Jan. 28, 2015 in U.S. Appl. No. 13/429,942 by Cabiri.
U.S. Appl. No. 14/593,041 by Cabiri, filed Jan. 9, 2015.
U.S. Appl. No. 14/683,253 by Cabiri, filed Apr. 10, 2015.
Office Action dated May 18, 2015 in U.S. Appl. No. 13/429,942 by Cabiri.
Office Action dated Oct. 28, 2015 in U.S. Appl. No. 13/429,942 by Cabiri.
Office Action dated Jan. 5, 2016 in U.S. Appl. No. 14/696,644 by Cabiri.
Office Action dated Dec. 3, 2015 in CN Application No. 201280068544.0.
Office Action dated Feb. 24, 2016 in U.S. Appl. No. 13/429,942 by Cabiri.
Office Action dated Jun. 1, 2016 in CN Application No. 2013800274556.
Office Action dated Jun. 17, 2016 in CN Application No. 201280068544.0.
Office Action dated Jul. 29, 2016 in U.S. Appl. No. 14/696,644, by Cabiri.
Search Report dated May 8, 2017 in EP Application No. 12750951.1.

* cited by examiner

TIME DEPENDENT DRUG DELIVERY APPARATUS

CROSS-REFERENCE TO RELATED APPLICATION

This application is a section 371 of International Application No. PCT/US2012/050696, filed Aug. 14, 2012, which was published in the English language on Aug. 8, 2013 under International Publication No. WO 2013/115843 which claims the benefit of U.S. Provisional Patent Application No. 61/592,978, filed Jan. 31, 2012, the disclosures of which are incorporated herein by reference.

BACKGROUND OF THE INVENTION

The present invention, in some embodiments thereof, relates to an apparatus and method for delivering a substance, more particularly, but not exclusively, to a disposable apparatus and method for delivering a drug to an unskilled and unsupervised recipient at a variable rate.

U.S. Pat. No. 5,957,895 to Sage relates generally to a device for delivering a liquid therapeutic preparation into the body of a patient by injection into or though the patient's skin, and more particularly, to a low-profile automatic injection device that can be worn inconspicuously under the clothing of a patient to allow a liquid therapeutic preparation (such as insulin) to be administered over an extended period of time, and that incorporates a self-emptying reservoir to eliminate the need for a pump or other type of discharge device.

U.S. Pat. No. 7,780,636 to Radmer relates to devices which are adapted for application to a skin surface of a user and comprise a transcutaneous device such as a needle or a needle-like member which is supplied in a sterile condition, as well as transcutaneous devices suitable for being used therewith. In specific aspects, the invention relates to transcutaneous devices adapted for insertion at a selected site within the body of a subject for subcutaneous, intravenous, intramuscular or intradermal delivery of a drug to the subject, the needles also being adapted for connection to a reservoir for containing a drug.

U.S. Pat. No. 5,997,501 to Gross discloses an intradermal drug delivery device comprising a housing having a drug reservoir therein. A microprocessor-controlled electrolytic cell provides gas to expand a gas generation chamber and thereby contract the reservoir. A hollow needle, communicating at an inner end thereof with the reservoir, extends from a lower surface of the housing such that contraction of the reservoir forces drug to escape therefrom for injection into a user via the needle. The device permits delivery of drugs of relatively large molecular weights at slow, controllable rates.

U.S. Pat. No. 7,918,843 to Genosar discloses a controllable drug delivery device for delivering a liquid injectable drug, the device comprising a drug reservoir, a drug delivery device, a displacement-generating battery, and a current-depletion circuit, wherein displacement generated by the battery as current is depleted from the battery by the current depletion circuit displaces a wall of the drug reservoir thereby causing the reservoir to expel liquid injectable drug contained therein via the drug delivery device, and wherein the drug delivery device further includes a controller that is responsive to a measured parameter indicative of displacement generated by the battery for applying a variable load across the battery in order to provide a substantially constant-current depletion of the battery and thereby cause the drug delivery device to deliver a substantially constant drug delivery rate.

U.S. Patent Application Publication No. 2011/0184342 and international patent application WO2009/081262 to Pesach, et al. disclose an apparatus and a system for controlling and/or managing administration of a drug to a body of a patient. The apparatus includes a drug infusion device configured to deliver drug at a predetermined location in the body of the patient, at least one sensor disposed in the drug infusion device and configured to measure a corresponding property related to the patient and selected from the group consisting of physiological properties, biochemical properties, environmental properties and drug-related properties, a controller disposed in the drug infusion device and configured to receive from the at least one sensor data representative of the measured corresponding property and based on the received data, determine a drug delivery rate. The drug delivery device is configured to deliver the drug to the body of the patient based on the determined drug delivery rate.

U.S. Patent Application Publication No. 2011/0178472 and international application WO 2011/090955 to the present author discloses A needle assembly adapted for fluid communication with a cartridge containing a substance to be delivered to a subject. The needle assembly is characterized by a biasing device arranged to apply a biasing force on a needle to cause the needle to protrude outwardly from a housing to, pierce the subject, and a biasing device release apparatus including a biasing device arrestor that initially blocks movement of the biasing device.

A safety latch position sensor is provided for sensing when a safety latch moves to an up position indicating that the device has been attached to a patient. A controller initiates operation of an actuator after a predetermined time delay (e.g., 5-15 seconds) to ensure that the drug delivery apparatus was indeed placed on purpose on the patient for delivering the drug. When operated, the actuator moves the biasing device arrestor out of an aperture. The actuator rotates a drive gear, which in turn rotates a spur gear to rotate a shaft. Rotation of the shaft causes the biasing device arrestor to move linearly out of the aperture along threaded portion. When the biasing device arrestor reaches the end of threaded portion, it rotates freely on a shaft and moves no further. As soon as the biasing device arrestor has, moved out of the aperture, the biasing device is no longer blocked and it now pushes on a needle, thereby piercing the patient's skin.

Additional background art includes U.S. Patent Application Publication No. 2011/0178472 to the same author, U.S. Pat. No. 6,530,901 to Tsukada, et al., and European Patent No. EP 0 744 975 to Knauer.

BRIEF SUMMARY OF THE INVENTION

Briefly stated, an embodiment of the present invention comprises an apparatus for delivering a drug to a recipient. The apparatus includes a transcutaneous device configured for insertion into a site within the recipient. A discharge mechanism is configured to deliver the drug via the transcutaneous device to the site. A processor is configured to control the discharge mechanism. A deactivation mechanism is configured to deactivate the apparatus once the drug has been delivered. A temperature sensor is configured to sense a temperature of one of a component of the apparatus or the drug. The processor is programmed to wait a predetermined period of time after activation before initiating the delivery of the drug, and is further configured to adjust the waiting time based on the temperature sensed by the temperature sensor.

Another embodiment of the present invention comprises an apparatus for delivering a drug to a recipient. The apparatus includes a transcutaneous device configured for insertion into a site within the recipient. A discharge mechanism is configured to deliver the drug to the site via the transcutaneous device. A temperature sensor is configured to sense a temperature of one of a component of the apparatus or the drug. A processor is configured to control the discharge mechanism and to adjust a rate of delivery of the drug according to the temperature sensed by the temperature sensor.

Yet another embodiment of the present invention comprises a method for delivering a drug to a recipient via a portable drug delivery device. The method includes inserting a transcutaneous device into a site within the recipient, delivering the drug to the site by the portable drug delivery apparatus via said transcutaneous device, and determining a rate of delivery of the drug based on a temperature of one of a component of the portable drug delivery apparatus or the drug.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according, to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard disk and/or removable media, for storing instructions and/or data. Optionally, a network connection is provided as well. A display and/or a user input device such as a keyboard or mouse are optionally provided as well.

The present invention, in some embodiments thereof, relates to an apparatus and method for delivering a substance, more particularly, but not exclusively, to a disposable apparatus and method for delivering a drug to an unskilled and unsupervised recipient at a variable rate.

In some embodiments, the apparatus may deliver the drug autonomously according to a time varying rate schedule. Optionally, there may be a time delay before drug delivery. Optionally the time delay and/or delivery rate may be adjusted according to the temperature of a component of the apparatus (for example the temperature of the drug and/or the temperature of a power source). In some embodiments, the recipient of the drug may be able to adjust the delivery rate and/or the time delay according to a preference (for example, to reduce pain induced by the injection). Optionally, the rate of delivery may be slower than a maximum rate of delivery. The maximum rate of delivery may be determined by one or more physiological imitations mechanical limitations' of the injection apparatus and/or regulatory limitations. For example, in some embodiments, the rate of delivery may be between 20% and 80% of the maximum rate of delivery.

In some embodiments, the maximum rate of delivery may optionally be between 10 ml/hr and 100 ml/hr. The total delivered volume may optionally be between 0.5 ml and 20 ml. The total time of delivery may be between 5 seconds and 20 minutes. In some embodiments, the total time of delivery may be measured from the beginning of delivery until the end of delivery. Optionally, the beginning of delivery may be measured from the time of activation of the apparatus and/or alternatively from the time of attachment of the apparatus and/or alternatively from the time that delivery of the substance actually begins. Optionally the end of delivery may be measured at deactivation of the apparatus and/or alternatively at the earliest time after which no more of the substance is delivered and/or alternatively when the apparatus is removed from the recipient.

Temperature Dependent Delivery

In some embodiments, the apparatus may be preprogrammed to wait a fixed time delay of 2-20 minutes after activation before beginning delivery of the substance. Optionally the length of the time delay may be an estimated time for a temperature sensitive component of the apparatus to reach a preferred working temperature. For example, the temperature sensitive component may include the drug and/or a battery.

In some embodiments, the apparatus may be stored under refrigeration at between 1° and 8° Celsius. Such cold temperatures may cause problems due to increased viscosity, reduced battery performance and/or increased pain for the recipient. An initial time delay before injection may allow heat from the recipient's body and/or from the air to warm up a temperature sensitive component to a preferred working temperature. In some embodiments, the preferred working temperature may optionally be between 10-37° Celsius.

In some embodiments, a sensor may be supplied to measure the temperature of the temperature sensitive component. For example, a thermocouple may be supplied to measure the temperature of the drug or the battery. Alternatively or additionally, the measured parameter may include a surrogate for the parameter of interest. For example, in some embodiments, the parameter of interest may be the temperature of the drug, but the temperature of the battery may optionally be measured. The temperature of the drug may be inferred from the temperature of the battery. In some embodiments, the voltage potential of the battery and/or the viscosity of the drug may be measured. The temperature of the battery and/or the temperature of the drug may be inferred therefrom.

In some embodiments, a delivery rate may be adjusted according to the temperature of the temperature sensitive component. For example, the delivery rate may be slowed when the apparatus is cold. The delivery rate may be increased as the apparatus warms up.

In some embodiments, a delivery schedule may be dependent on multiple factors. For example, there may be a preprogrammed time delay and/or a sensor to detect if the apparatus is properly in contact with the subject and/or one or more temperature sensors to test a temperature of the substance being delivered and/or the temperature of a battery. For example, delivery may start after the time delay only if the batteries have reached a certain temperature and the delivery rate may be dependent on the temperature of the substance.

Recipient Modified Delivery

In some embodiments of the present invention, the delivery rate and/or time delay may be adjusted by a recipient during delivery of the substance. For example, a recipient of an injecting drug pump may desire to lower the injection rate. For example, reducing the injection rate may reduce the pain of the injection. In some cases, a recipient of a drug may want to get the treatment over more quickly by increasing the delivery rate.

In some embodiments, recipient adjustments to the time delay and/or delivery rate may be limited. For example, the recipient may be able to slow the delivery rate up to 50% or increase the delivery rate up to 200% of the preferred rate. Optionally, a user input interface may be supplied, by which a caretaker and/or the recipient of the medication can adjust the delivery rate.

Delivery following a Time Delay after a Medical Procedure

In some embodiments of the present invention, the apparatus may be programmed with a time delay recommended for delivery of a medicine after a medical procedure For example, sometimes follow up to a medical procedure entails injection of a drug at a prescribed time after the procedure. Optionally, an apparatus may be activated and/or attached to a recipient while the recipient is undergoing a supervised medical procedure. Optionally the apparatus may be programmed to wait the prescribed time and then deliver the drug to the recipient at the prescribed time. In some embodiments, the time delay may be between 1 hour and 48 hours. Optionally, the injection time may be defined in terms of an elapsed time or as an absolute time (e.g. a time of day and/or a scheduled hour).

Portability

In some embodiments, the apparatus will minimally disturb the recipient. For example, the apparatus may be small and light. Optionally the apparatus may be worn by the recipient. Wearing the apparatus may include, for example, attaching the apparatus to the recipient and/or carrying the apparatus attached to clothing of the recipient and/or strapping the apparatus to the recipient. For example, the apparatus may stick to the skin of the recipient (for example via an adhesive). Optionally, the apparatus may not require conscious carrying by the recipient.

Optionally, the apparatus may be less than 5 cm long and/or less than 5 cm wide and/or have a thickness of less than 3 cm. Optionally, the total volume of the apparatus may be less than 100-200 ml. Optionally, the mass of the entire apparatus with the substance may be less than 100-200 g. Optionally, the capacity of the reservoir for the substance in the apparatus may be between 5-30 ml). Optionally, the apparatus may be shock proof and/or waterproof. The term "reservoir" throughout the specification and claims encompasses any container for a drug, such as but not limited to, a cartridge, vial, syringe, bottle, ampoule and many more, and is not limited to any size or shape.

Before explaining at least one preferred embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Timelines

Delivery of a Drug after a Medical Procedure

Figures 1A, 1B:
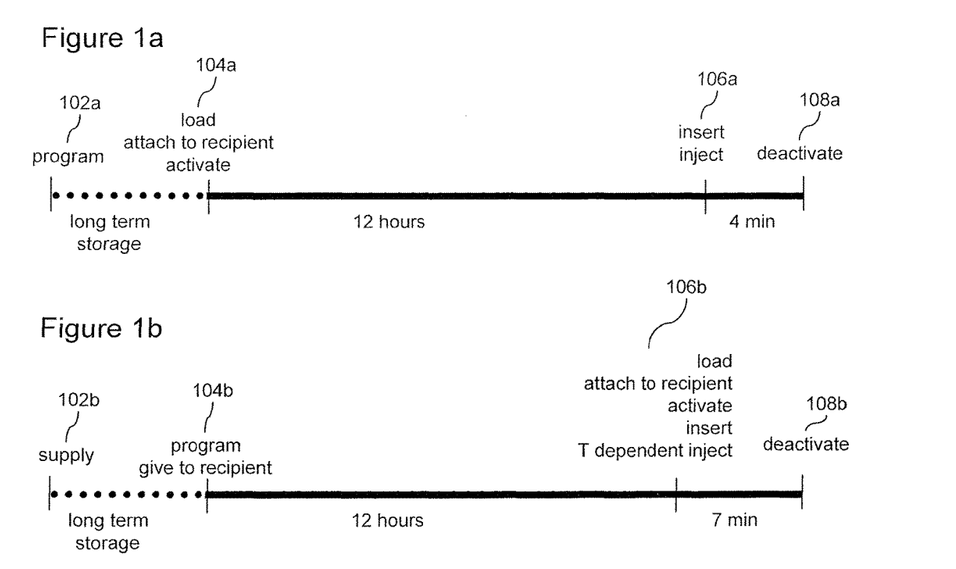
FIG. 1a is a time line illustrating a first preferred embodiment of the present invention.
FIG. 1b is a time line illustrating a second preferred embodiment of the present invention.
Figure 1C:
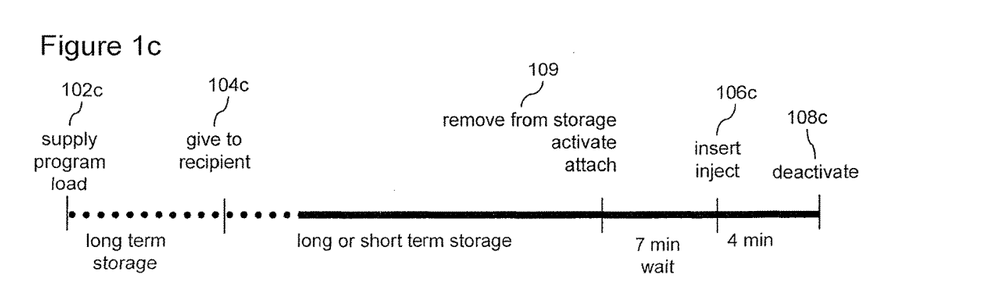
FIG. 1c is a time line illustrating a third preferred embodiment of the present invention.

FIGS. 1a-c are time lines illustrating a few examples of how a one-use time dependent drug delivery apparatus may be used. In the examples of FIGS. 1a-c, a patient (the recipient) needs a drug injection a few hours after an outpatient medical procedure.

In some embodiments, the apparatus is a medicine pump. The invention is not limited to a drug pump, and may be used for any kind of suitable discharge apparatus, not just by needle piercing the patient, but by spray (wherein the substance is metered by apparatus to a spray nozzle), micro needles array and others.

Delivery of Medicine without Supervision

In the example, the patient prefers to return home and not remain in an institution waiting for a nurse to administer the injection. The recipient is supplied with a portable apparatus that optionally autonomously delivers the medicine to the recipient even at a remote location (for example the patient's home or while outside taking a walk) without requiring supervision (for example by medical personnel and/or an alert recipient). Optionally the delivery may take place as scheduled even if the recipient has fallen asleep. In the examples of FIGS. 1a-c, 4 ml of fluid is to be injected.

Recipient May Have Limited Capabilities

In some cases, the recipient may be incapable of taking responsibility for his own treatments. For example, the recipient may include a child and/or the medical procedures may induce fatigue or confusion in the recipient (for example chemotherapy).

Programming by a Supplier; Loading and Attachment by a Prescribing Institution

In the exemplary embodiment of FIG. 1a, the medication to be injected is optionally packaged in a sealed vial by a drug distributer. The injector is optionally supplied 102a in a programmed state by supervisory personnel at the distributor. The distributor optionally programs the injector with a waiting period before delivery of the drug after a medical procedure. Optionally, the distributer packages the injector separately from the medication.

For example, in the exemplary embodiment the substance to be injected is an antidote to a chemotherapy agent. The substance is to be injected twelve hours after the therapy. Optionally, the distributer also prepares an injector to deliver the antidote 12 hours after activation. The injector and the medicine may optionally be, packaged separately. In the example, the drug and injector are sold together to the medical institution with instructions for medical personnel.

In the example of FIG. 1a, the drug and injector may optionally be stored until needed by a medical institution. Optionally the drug and the injector may be stored together or separately. The storage may optionally be for a few days or up to a year or a few years.

In the example of FIG. 1a, when the injector is needed, the medical institution optionally loads the medication into the injector, activates the injector and attaches the injector to a recipient 104a (in various embodiments as explained below activation may be before or after loading). Optionally, once attached, the injector may be free standing in that it may function without connection to external resources (for example external power supplies, an external drug reservoir and /or an external control unit).

In the example, the antidote is loaded into the injector and the injector activated immediately following the chemotherapy treatment. Once activated, the injector may be attached to the patient at a convenient time after the treatment. For example, the injector may be attached to the recipient immediately after the procedure or later, just before he leaves the medical institution.

In further optional examples, the injector may optionally be programmed with a time delay that is a couple of hours longer than the waiting period between the end of the procedure and the optimal injection time. In such a case medical personnel may activate the injector and/or attach it to the recipient before starting the procedure.

In the example of FIG. 1a, after the injector is attached, the recipient may optionally leave the supervision of the medical institution. For example, the recipient may go home. The injector autonomously delivers 106a the medicine at the end of the prescribed waiting period (in the exemplary embodiments of FIGS. 1a-c the drug is to be take 12 hours after a medical procedure). The recipient receives the proper medication at the proper time even if he has fallen asleep and/or forgotten and/or is not qualified and/or is unable to give himself an injection. Optionally, the injector may warn the recipient (for example via an audible alarm or by vibrating) before injection starts.

In the example of FIG. 1a, injection starts 12 hours after activation of the injector. At the beginning of injection, the medicine has already equilibrated to a temperature between room temperature and the skin temperature of the recipient. Injection starts immediately at a preferred rate of 60 ml/hr until the entire prescribed dosage (4 ml) is injected (in the example of FIG. 1a 4 ml is injected at a rate of 60 ml/hr for 4 min).

Conventionally it is often preferred to inject at a rate near the highest safe rate of injection. The highest safe rate of injection rate may be limited by set mechanical limitations of the injection device and/or physiological limitations of the patient and/or regulatory standards. Using a high rate of injection reduces the time of the injection and may reduce the possibility of mishaps interfering with the injection process.

After injection is finished, the injector optionally deactivates 108a itself. Deactivation 108a may optionally protect from misuse or mishaps. Optionally, deactivation 108a may include permanently disabling the delivery apparatus. In some embodiments, deactivation may make the injector compliant with municipal garbage requirements allowing disposal of the injector in the municipal garbage.

For example, in some embodiments, the injector is deactivated 108a by protecting the injector needle. Protecting the injection needle may prevent accidental needle sticks. For example, garbage collectors may be protected from needle sticks from the deactivated, apparatus. Needle protection may include, for example, retracting a needle and/or automatic deployment of a needle cover to cover the protruding needle. Optionally, deactivation may be triggered automatically after delivery of the prescribed volume of substance and/or dependent on an action, for example when the apparatus is removed from the recipient as is explained herein below.

In some embodiments, a drug delivery apparatus may be configured to automatically deactivate and/or warn the recipient when a malfunction occurs. For example, the apparatus may autonomously permanently deactivate when it is instructed to deliver the substance while not properly attached to a recipient, and/or it may deactivate when the battery power is too low.

Programming at a Prescribing Institution; Loading and Attachment by the Recipient FIG. 1b shows a second optional time line for use of an injector according to the present Invention. In the example of FIG. 1b, the injector is supplied 102b to the medical institution in an un-programmed state. In the example, supervisory personnel at the medical institution program the injector according to the needs of the recipient and give the injector and the medicine to the recipient 104b.

In some embodiments, the apparatus may be programmed to deliver the medicine immediately on activation (the recipient being trusted to attach and activate the apparatus at the right time). Optionally, the apparatus may be programmed with a time window. If the recipient activates the apparatus too early, the apparatus waits until the prescribed time before delivering the substance. Optionally, if the recipient forgets to activate the apparatus; an alarm may ring, reminding him to attach and activate the apparatus. If the recipient activates the apparatus too late, then an error condition occurs. Alternatively or additionally, the recipient and/or a medical supervisor may be alerted when an error condition occurs (for example activation of the apparatus that is too late). Alternatively or additionally, a medical supervisor may contact the recipient (for example by phone) to remind him to attach the apparatus and/or to make sure that the medicine was properly delivered.

In some embodiments, the recipient stores the injector with the medicine until the time prescribed by the doctor. Just before the prescribed time, the recipient removes the injector from storage, loads the medicine, attaches the injector to his body and activates the injector.

In the embodiment of FIG. 1b, upon activation, a hypodermic needle is inserted into the recipient. The substance is then injected 106b. Optionally, the rate of injection is a function of the temperature of the substance being injected. In this example, the recipient had stored the medicine in a refrigerator and did not let it warm to room temperature before loading and activating the injector.

The cold temperature may have undesired consequences. For example, medicine may increase in viscosity as the temperature drops. Pushing cold highly viscous medicine at a high rate through a thin hypodermic needle requires a large force and places a correspondingly large stress on the pump mechanism. High stress may inc ease the probability of mechanical failure of the apparatus. Cold batteries may produce less current and/or last less time than warm batteries. Cold batteries may not be able to produce enough power to pump a cold viscous medicine at a high rate. Failure to pump the medicine at the prescribed rate may cause the apparatus to shut down. Some patients experience more pain when a cold medicine is injected as compared to when the medicine is injected at room temperature or body-temperature.

Some of the negative effects of cold may be mitigated by reducing the injection rate. For example, the injection rate may be reduced to a rate much less than the maximum and/or preferred injection rate determined for a room temperature drug and/or injector.

Figure 3A:
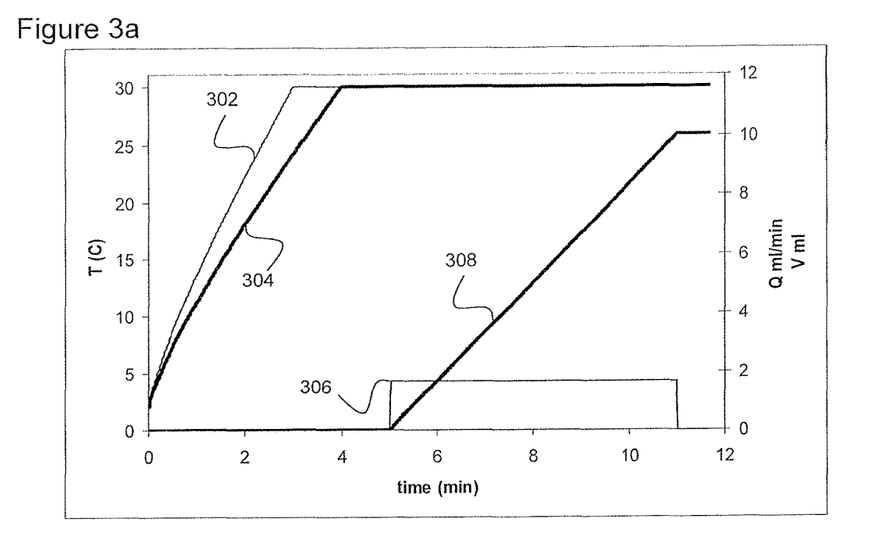
FIG. 3a is a graph of time versus temperature and delivery rate and volume of a preferred delayed injection according to the invention.
Figure 3B:
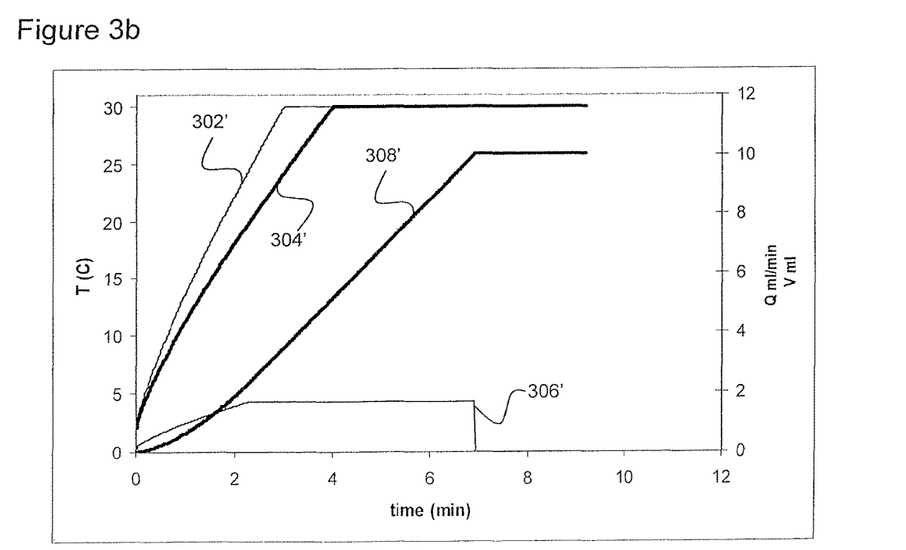
FIG. 3b is a graph of time versus temperature and delivery rate and volume of a preferred variable rate injection according to the invention.

Optionally, the injection rate will, for example, be less than the preferred rate (60 ml/hr) at the beginning of injection while the medicine is cold (for example see FIG. 3b). The slow rate of injection over part of the injection period causes an increase in the injection time. In the example of FIG. 2b, injection 106b ends when a predetermined volume (4 ml) has been injected after 7 minutes of injection. After injection 106b ends, the injector is autonomously deactivated 108b.

Programming and Loading by a Supplier, Attaching and Activating by a Recipient

FIG. 1c illustrates a third exemplary timeline for use of the present invention. In the third example, the apparatus is optionally supplied 102c, programmed and loaded by a distributor. The medicine and injector are stored together and sold to a medical institution and/or a pharmacy. The loaded injector is given 104c and/or sold to the recipient.

The recipient stores the injector and the medicine until the prescribed injection time. Upon reaching the prescribed injection time, the recipient removes the injector from storage 109, activates the injector and attaches it to his skin.

After activation and attachment, the injector optionally waits a programmed time delay and autonomously starts injection without further action from the recipient. In the example, of FIG. 1c, the programmed time delay is 7 minutes, which is an estimated time necessary for the medicine to warm up from a storage temperature to a preferred injection temperature (see for example FIG. 3a). After the waiting period, the medicine is injected 106c at a preferred rate of 60 ml/hr for 4 minutes until the prescribed dose of 4 ml has been delivered. After injection, the injector deactivates 108c itself.

A Simplified Example of a Medicine Delivery Apparatus

Figure 2:
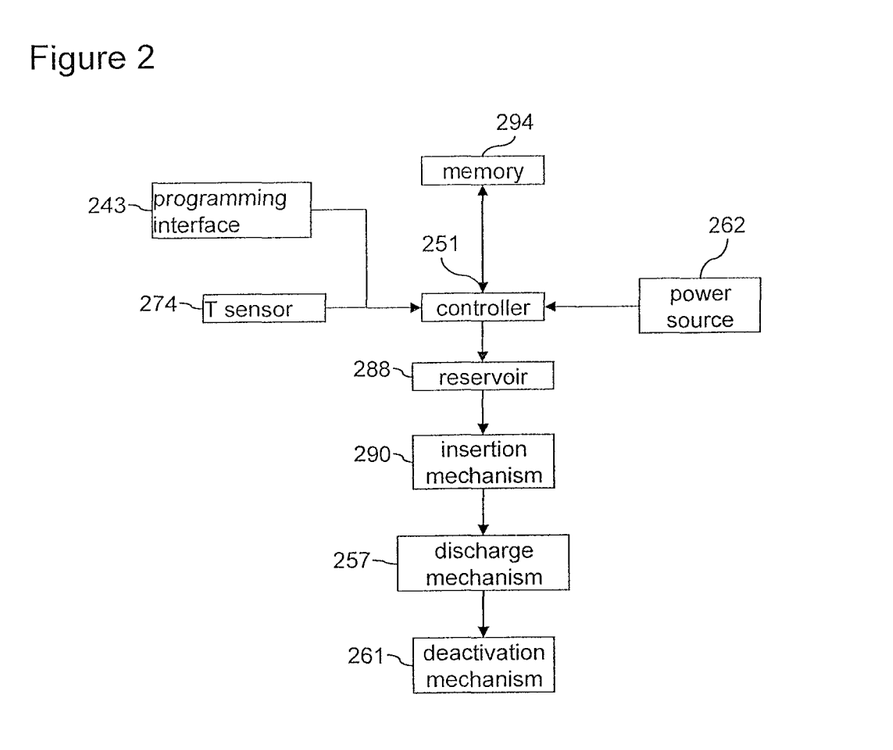
FIG. 2 is a simplified functional block diagram of a preferred embodiment of the present invention.

FIG. 2 is a simplified schematic block diagram illustration of an exemplary embodiment of a drug delivery apparatus. The exemplary apparatus is configured to simplify home delivery of a drug. The drug is stored in a reservoir 288. A controller 251 manages the delivery rate of a drug by a discharge mechanism 257 according to output of a temperature sensor 274 and/or instruction programmed into a memory 294. Optionally, programming is performed using a programming interface 243 (for example using an interface cradle) that is only available to qualified personnel. For example, supervisory health personnel may program the apparatus. Optionally recipient of the apparatus may be prevented from changing the program.

In some cases, the apparatus or a component thereof (in this context the power source 262 or batteries and the substance to be delivered are considered components of the delivery apparatus) will be stored in cold storage. Controller 251 is optionally programmed to delay delivery long enough for the component to warm up. For example, instructions may be stored in memory 294 to wait 3-20 minutes after activation of the apparatus before starting delivery of the substance. Alternatively or additionally, instructions may be stored in memory 294 for ramping up a delivery rate over time.

In some embodiments, the delivery rate may be adjusted according to a measurement of temperature sensor 274. In some embodiments, one or more temperature sensors 274 may measure the temperature of reservoir 288, the temperature of a battery 262 and/or the temperature of other components of the delivery apparatus.

Other aspects of the delivery may be automated and/or handled by controller 251 and/or synchronized with delivery of the substance. For example, there may be an optional insertion mechanism 290 for insertion of a needle into the skin of a recipient. Inserting the needle may open a pathway for delivering the medicine. Insertion may be delayed until after at least half of the waiting period.

There may be an optional deactivation mechanism 261. Deactivation mechanism 261 may deactivate the apparatus after a prescribed quantity of substance has been delivered and/or upon removal of the apparatus from the skin of the patient.

Graphs of Time Dependent Temperature and Delivery Rate

FIG. 3a and FIG. 3b are graphs illustrating two exemplary embodiments of delivery schedules and time dependent temperatures of components of a delivery apparatus. Many substances are stored at low temperatures (for example in a refrigerator). In some cases, a preloaded delivery apparatus and the medicine that it contains may optionally be stored together in a refrigerator.

In the exemplary embodiments of FIGS. 3a and 3b, the substance to be delivered is 10 ml of fluid to be delivered at a maximum rate of 100 ml/hr. In the example, the delivery apparatus is stored in a refrigerator at 2° Celsius. At time "t=0" the delivery apparatus and preloaded substance are removed from the refrigerator. The starting temperature of the batteries and the substance to be delivered is 2° C.

The delivery apparatus is activated shortly after removal from the refrigerator. In the examples of FIGS. 3a and 3b, after activation the delivery apparatus is stuck to the skin of a recipient. While the delivery apparatus is stuck to the recipient's body, heat from the recipient's body and the air slowly warm the delivery apparatus including the batteries and the substance to be delivered. Eventually, the temperature of each component equilibrates to a temperature less than the skin of the subject and greater than room temperature. Once the temperature has equilibrated, it remains substantially constant.

Delivery at a Constant Rate after a Time Delay

FIG. 3a illustrates an embodiment of a delivery apparatus with an optional fixed time delay. During the time delay, the delivery rate is zero. After the delay, delivery starts at a finite constant rate. In FIG. 3a, time in minutes is shown on the abscissa and temperature in degrees Celsius on the left ordinate axis. The right ordinate axis shows flow rate and cumulative flow volume in ml/min and ml respectively. Associated with the left ordinate axis are the time dependent battery temperature 302 and medicine temperature 304 (the substance to be delivered) inside a delivery apparatus. Associated with to the right ordinate axis are the cumulative delivered volume 308 and instantaneous delivery flow rate 306.

Fixed Schedule

In the exemplary embodiment of FIG. 3a, the initial temperature of the medicine and battery are both approximately 2° Celsius. The delivery apparatus is programmed to optionally wait five minutes after activation and then optionally deliver at the maximum rate until the prescribed volume has been delivered. It is estimated that within five minutes the recipient's the air will heat the medicine to at least a working temperature of 10° C. At the working temperature, the pump mechanism can safely pump the medicine at the desired injection rate.

Maximum Delivery Rate

In some embodiments, the maximum rate of delivery may depend on the medicine being delivered. For example, substances that are more viscous may be injected more slowly and/or substances that cause greater pain may be delivered more slowly. Optionally, the maximum delivery rate may be programmed into the delivery apparatus by the supplier. Optionally, the maximum delivery rate may depend on the patient. For example, for a child, the maximum delivery rate may be less than an adult, or the patient may express a preference for longer, less painful injections. Optionally, the optimal delivery rate may be programmed into the apparatus by medical personnel.

Temperature Dependent Delivery Rate

FIG. 3b is a graph illustrating an exemplary embodiment of a delivery rate that is dynamically dependent on the temperature of the substance being delivered. Time in minutes is shown on the abscissa and temperature in degrees Celsius on the left ordinate axis. The right ordinate axis shows flow rate and cumulative flow volume in ml/min and ml respectively. Associated with to the left ordinate axis are the time dependent battery temperature 302' and medicine temperature 304' (the substance to be delivered). Also shown are the cumulative delivered volume 308' and instantaneous delivery flow rate 306'.

Insertion

In the exemplary embodiment of FIG. 3b, the delivery apparatus includes a temperature sensor that detects the temperature of the substance to be delivered. In the example, the delivery apparatus is optionally programmed to insert a needle into the recipient after activation and attachment.

Delivery at a Temperature Dependent Rate

Optionally after insertion, delivery starts immediately at a rate that is dynamically adjusted based on a measurement of a temperature sensor. In the example, the delivery rate is linearly proportional to the medicine temperature up until the maximum rate. Delivery stops when the prescribed volume has been delivered. Temperature dependent delivery rate may allow a shorter total operating time than a fixed time delay, while still protecting the mechanism and recipient from high rate delivery of a cold substance.

In some embodiments, the delivery rate may be a complex function of time, for example, there may be a delay period with zero delivery rate. Additionally and/or alternatively, there may be a ramp up period where delivery rate increases as a function of time (optionally in a time period the relation between delivery rate and time may be linear and/or non-linear). Optionally, there may be a period of delivery at a maximum rate.

In some embodiments, the delivery rate may be dependent on an estimate of the medicine temperature. Optionally, the delivery rate may be ramped up based on the estimated temperature without requiring a temperature sensor. Optionally, the delivery rate may be chosen for an unlikely bad case scenario. For example, delivery rate may be slowly ramped up according to the estimated preferred rate for a drug warming up from an initial temperature between −5° to +10° Celsius and/or in a cold atmosphere of between −10° and +10° Celsius and/or on a recipient having a low body temperature of between 29° to 37° Celsius. Alternatively or additionally, the delivery rate may be change in time according to a typical scenario. For example, the delivery rate may be ramped up over time according to a preferred rate for the case of a drug starting at between 2° to 25° Celsius in a room at between 20° to 30° Celsius with the recipient body temperature of between 36° to 38° Celsius.

A Method and Apparatus Illustrating Optional Features

Figure 4:
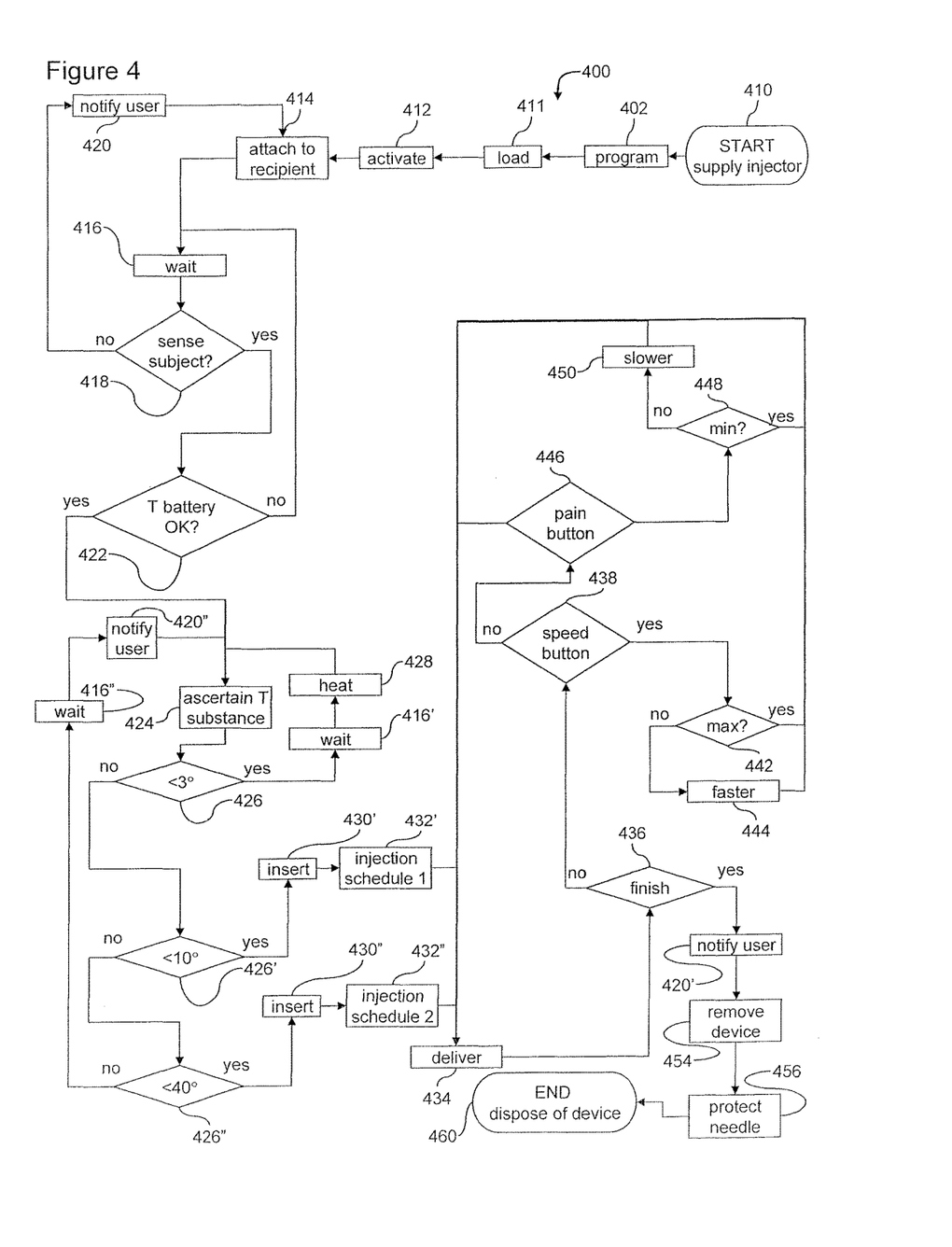
FIG. 4 is a flow diagram chart illustrating a preferred embodiment of a method according to the invention.
Figure 5:
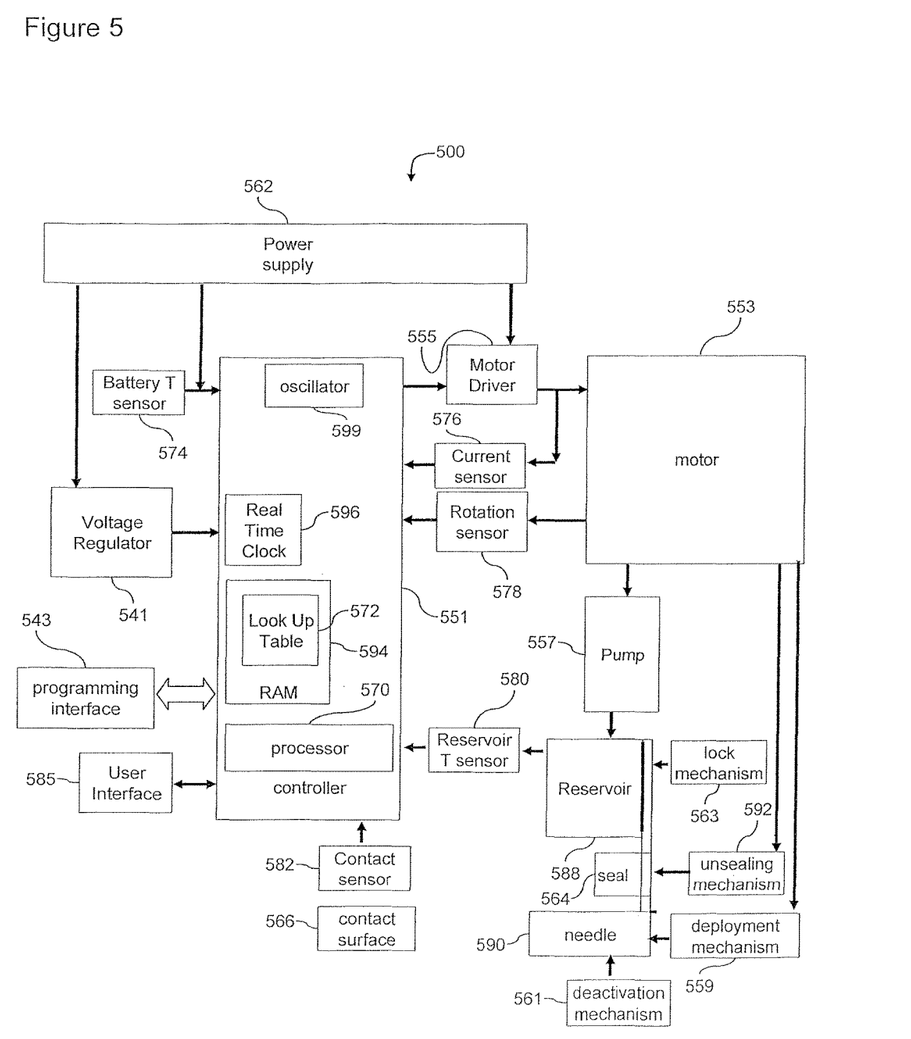
FIG. 5 is a schematic block diagram of another preferred embodiment of the invention.

FIGS. 4 and 5 illustrate an exemplary embodiment of a method and disposable single-use apparatus for delivering a substance at a variable rate. FIG. 4 is a flow diagram illustrating an exemplary embodiment of a method of delivering a substance at a variable rate 400. FIG. 5 is a schematic block diagram of an exemplary embodiment 500 of a disposable apparatus for variable rate delivering of a substance.

Time Delay Dependent on a Look up Table

In the exemplary embodiment of FIGS. 5 and 6, the delivery rate may change over time after activation due to various factors. Optionally there may be a lookup table containing one or more predefined delivery schedules. A particular schedule may be selected according to various delivery conditions including for example the output of one or more sensors as illustrated below.

In the exemplary embodiment of FIGS. 5 and 6, there may be two separate interfaces: a user interface 585 and a programming interface 543.

Embodiment 500 includes an optional mount for a programming interface 543, which may include a communication cradle. The communication cradle may be used, for example, for programming controller 551 before assembly of the apparatus. In some embodiments, a wireless connection may be used for programming controller 551.

In some embodiments, programming interface 543 will include a communication cradle that attaches to the assembled apparatus. For example, the apparatus may be programmed 402 by medical personnel and/or by personnel at the manufacturer. Attachment of the cradle to the delivery apparatus may employ known connectors, for example a USB or a ZIGBEE connector.

In some embodiments, the apparatus may include a wireless connection to a cellular network. Notification may be sent to the recipient of the medication and/or to a caretaker (for example a nurse and/or a family member) and/or to a doctor in case of a malfunction. For example, notification 420 may include one or more of the following:

an audible notification—for example an alarm or a synthesized voice message;
lighting of a light (for example an LED);
a written message on a display;
a symbolic message on a display (for example an icon);
a text message over a wireless connection (for example via a remote control unit or an SMS over a wireless network);
a non-text message over a wireless connection.

In some embodiments, programming interface 543 may be available only to a professional programmer. An optional, separate user interface 585 may be provided for use by the recipient or his caretaker.

In some embodiments, user interface 585 will be very simple. A simple user interface 585 may, protect the recipient and/or caretakers from accidents and/or mishaps. Optionally, a simple user interface 585 may include an activator and/or a pain button (for example a button that a recipient can press in order to reduce the rate of delivery thereby reducing his pain). Optionally, a simple user interface 585 may include a light emitting diode LED (for example a red LED which warns of a malfunction) and/or a liquid crystal display LCD for showing simple messages.

In the exemplary embodiment, a preloaded apparatus is supplied 410 for variable rate delivery of a substance. Optionally, supplying the delivery apparatus may include loading 411 the apparatus with a medication. Exemplary embodiment 500 includes an optional lock mechanism 563. After the delivery apparatus is loaded 411, lock mechanism 563 prevents further tampering with the delivery apparatus or the substance to be delivered.

In the exemplary embodiment of FIGS. 4 and 5, the delivery apparatus is activated 412 and attached 414 to a recipient of the substance (for example a patient needing the drug). In some embodiments, activation 412 may be subsequent to attachment 414. For example, a recipient may first attach 414 the apparatus and then activate 412 it by pushing a button.

In the exemplary embodiment of FIG. 4, the delivery apparatus waits 416 an optional set time delay after activation 412. Some embodiments may not include an initial waiting 416 period.

Preliminary Tests

Optionally, embodiment 500 may include of preliminary tests to make sure that the apparatus is properly attached and ready to function. Some embodiments may contain one or more of the tests and sensors found in exemplary embodiment 500.

After waiting 416, an optional attachment sensor 582 tests whether the apparatus is attached properly 418 to the skin of the subject. For example, an attachment sensor may include one or more of the following:

an optical sensor—for example, if the apparatus is properly attached, the optical sensor should be blocked by skin and not detect any light;

a temperature sensor for detecting body heat;

an electrical resistance sensor—for example, two electrodes may extend from the face of the apparatus to contact the skin of the recipient when the apparatus is attached; if the resistance between the electrodes is in the range human skin then attachment is confirmed;

a pressure sensor.

If the apparatus is not attached properly 418 then the user (for example the recipient and/or a caretaker) is notified 420. In the exemplary embodiment, user may then reattach 414 the apparatus. In some embodiments, improper attachment will cause an error and require a supervisor to reactivate the apparatus.

Some embodiments may include a power supply 562. In the exemplary embodiment, power supply 562 includes one or more batteries. An optional battery temperature sensor 574 checks the battery temperature 422. If the battery temperature 422 is not acceptable then the apparatus waits 416 for the batteries to equilibrate. Optionally, if the battery temperature is too high, the apparatus may inform a user that there is a malfunction. Delivery proceeds when the battery temperature 422 is within an acceptable range (for example between 10°-40° C.).

In some embodiments, a hypodermic injection needle 590 will be inserted into the patient immediately upon activation 412 and/or attachment 414 of the delivery apparatus; in some embodiments, insertion 430', 430" of the needle will not be initiated until the end of a delay period. An insertion mechanism 559 is optionally powered by motor 553. Optionally, a deployment mechanism may be powered by a spring-loaded mechanism and/or by a force applied by a user (for example the recipient, his caretaker, or medical personnel).

Look up Table Example

In exemplary embodiment 500, inserting 430', 430" needle 590 and delivery of the substance are optionally dependent on a delivery schedule. In the exemplary embodiment, a look up table 572 is provided having various optional delivery schedules. A delivery schedule may optionally be selected from a look up table dependent on the output of one or more of the sensors.

In the exemplary embodiment, a delivery schedule is selected according to the measured 424 substance temperature. For example:

If the temperature is less than 3° C. 426 then delivery is delayed 416' until the substance warms up. Optionally, the substance to be delivered may also be heated 428, for example using a chemical heater.

If the temperature of the substance is equal to or greater than 3° C. 426 but less than 10° C. 426', then look up table 572 outputs a first delivery schedule 432'.

If the temperature of the substance is greater than 10° C. 426' but less than 40° C. 426", then look up table 572 outputs a second delivery schedule 432".

If the temperature is over 40° C. 426" then injection may optionally be delayed 416" and the user may be optionally be notified 420" of the unusually high temperatures. The user may try to ascertain what is the cause of the problem (for example was the delivery apparatus left in the sun and/or does the recipient have a fever).

For example, in first delivery schedule 432', delivery 434 may start slowly and increase over time (allowing the substance warms). In the exemplary embodiment, the second delivery schedule 432" may call for delivery 434 at a maximum rate. In either case, delivery 434 continues until the prescribed 10 ml of fluid has been finished 436.

User Control of Injection Speed

In the exemplary embodiment, the user can control the rate of delivery of the substance. For, example, the user input interface 585 may optionally include a speed 438 button and a pain 446 button. During delivery, when the user pushes the speed 438 button, the apparatus will check the current delivery rate. If the current delivery rate is less than the maximum 442 then the delivery rate of the substance is increased 444. In the exemplary embodiment, if the maximum 442 rate has already been reached, then the, speed button is ignored. In some embodiments the maximum rate may be a fixed value (for example a maximum rate for intradermal injection may be between 50-100 ml/hr) and/or the maximum rate may be fixed as a percentage of the preferred rate (for example the maximum rate may be 150-200% of the preferred rate).

During delivery of the substance, when the user pushes the pain 446 button, the apparatus will check the current delivery rate. If the current delivery rate is greater than the minimum 448, then the delivery rate of the substance is decreased 450. In the exemplary embodiment, if the minimum 448 rate has already been reached, then the pain button is embodiments the minimum rate may be a fixed value (for example a minimum rate for intradermal injection may be between 5-20 ml/hr) and/or the minimum rate may be fixed as a percentage of the preferred rate (for example the minimum rate may be 20-50% of the preferred rate).

Controller and Motor Driver

Embodiment 500 includes a controller processor 570. In the exemplary embodiment, processor 570 controls the rate of delivery of the substance. In embodiment 500, controller 551 coordinates activity of the delivery apparatus. In the exemplary embodiment, controller 551 includes optional components: for example a random access memory 594, a real time clock 596, and an oscillator 599. Some embodiments may optionally include one or more of these components. Embodiment 500 includes a motor driver 555. In the exemplary embodiment, Controller 551 controls motor 553 using pulse width regulation. Embodiment 500 includes an optional voltage regulator 541. Voltage regulator 541 ensures that the input voltage to controller 551 remains steady even when the voltage of power source 562 varies.

Some embodiments may include an alternative motor and drive mechanism. For example, some embodiments may include a stepper motor in place of or along with the DC motor and PWM driver.

In the exemplary embodiment, motor 553 powers a discharge mechanism, pump 557. Optionally pump 557 causes pressure inside reservoir 588. When reservoir 588 is unsealed (for example after puncturing of seal 564 by an unsealing mechanism 592), pressure may cause fluid from reservoir 588 to be discharged through hypodermic needle 590 and delivered 434 to the recipient.

In some embodiments, pump 557 may include an optional syringe with a plunger. In some embodiments pump 557 may be driven by other mechanisms such as release of pressurized materials and/or expansion of materials and/or squeezing by an elastic material.

Deactivate

In the exemplary embodiment, when delivery is finished 436, the user is optionally notified 420' that delivery of the medicine is complete. Exemplary embodiment 500 includes an optional deactivation mechanism 561. After delivery, deactivation mechanism 561 deactivates the delivery apparatus. Optionally deactivation may prevent improper reuse. In exemplary embodiment 500, deactivation mechanism 561 optionally includes protecting 456 needle 590 preventing unintentional needle sticks.

In some embodiments, needle 590 will be protected 456 at the end of delivery 434. Optionally, protection 456 may be automatic and/or as a result of some action of the user. For example, in some embodiments, removal 454 of the apparatus by the user will trigger protection 456 of the needle. In some embodiments, the needle may remain in the recipient ready for another delivery. In some embodiments, the needle may be retracted and/or bent and/or broken and/or covered.

In the exemplary embodiment, after a single-use, once all the substance has been delivered, the user disposes 460 of the apparatus in the municipal garbage.

It is expected that during the life of a patent maturing from this application many relevant technologies will be developed and the scope of the terms is intended to include all such new technologies a priori.

As used herein the term "about" refers to ±10%.

The terms "comprises", "comprising", "includes" "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A drug delivery apparatus, comprising:
   a drug reservoir that stores a drug therein;
   a temperature sensitive component that is at least one of the drug, the drug reservoir, or a power source that powers the drug delivery apparatus;
   a temperature sensor in thermal communication with the temperature sensitive component to sense a temperature of the temperature sensitive component;
   a transcutaneous device; a pump coupled to the transcutaneous device to deliver the drug via the transcutaneous device; and
   processor that:
   (i) receives from the temperature sensor an initial sensed temperature of the temperature sensitive component prior to initial delivery of the drug,
   (ii) calculates a time delay for the temperature sensitive component to reach, starting from the initial sensed temperature, a predetermined working temperature that is between 100 C and 37° C., and (iii) initiates initial delivery of the drug by the drug delivery apparatus following expiration of the calculated time delay, regardless of the temperature of the temperature sensitive component following expiration of the calculated time delay.

2. The drug delivery apparatus of claim 1, wherein the temperature sensitive component is one of the drug, the power source, or the drug reservoir.

3. The drug delivery apparatus of claim 1, wherein the processor controls delivery rate of the drug based upon an output of the temperature sensor.

4. The drug delivery apparatus of claim 1, further comprising a memory coupled to the processor.

5. The drug delivery apparatus of claim 4, wherein the processor controls delivery rate of the drug by the pump based upon output of the temperature sensor and instructions programmed into the memory.

6. The drug delivery apparatus of claim 4, further comprising a programming interface coupled to the memory.

7. The drug delivery apparatus of claim 1, further comprising an insertion mechanism coupled to the transcutaneous device and controlled by the processor to insert the transcutaneous device.

8. The drug delivery apparatus of claim 1, further comprising an insertion mechanism controlled by the processor to insert the transcutaneous device after the calculated time delay.

9. The drug delivery apparatus of claim 1, further comprising a deactivation mechanism deactivating the apparatus after delivery of at least a prescribed quantity of the drug.

10. The drug delivery apparatus of claim 9, wherein the deactivation mechanism performs at least one of protecting a needle, preparing the apparatus for disposal, or permanently disabling the apparatus.

11. The drug delivery apparatus of claim 1, further comprising a user interface that is operable to decrease and increase a rate of drug delivery.

12. The drug delivery apparatus of claim 11, wherein the user interface is operable to increase the rate of drug delivery up to about 200%.

13. The drug delivery apparatus of claim 11, wherein the user interface is operable to increase the rate of drug delivery up to about 50%.

14. The drug delivery apparatus of claim 1, further comprising a heater that heats at least one component of the drug delivery apparatus or the drug.

15. The drug delivery apparatus of claim 1, wherein the predetermined working temperature is room temperature.

16. The drug delivery apparatus of claim 15, wherein room temperature is between 20° C. and 30° C.

17. A portable drug delivery apparatus configured to be attached against the skin of a recipient for delivering a drug to the recipient, comprising:
   a temperature sensitive component that is at least one of a drug to be delivered to the recipient or a power source that powers the drug delivery apparatus;
   a temperature sensor in thermal communication with the temperature sensitive component to sense a temperature of the temperature sensitive component;
   a transcutaneous device; a pump coupled to the transcutaneous device to deliver the drug via the transcutaneous device; and
   a processor that:
      (i) receives from the temperature sensor an initial sensed temperature of the temperature sensitive component prior to initial delivery of the drug,
      (ii) calculates a time delay for the temperature sensitive component to reach, starting from the initial sensed temperature and based a heat transfer from at least one of the skin of the recipient and air in proximity to the drug delivery device to the temperature sensitive component, a predetermined working temperature that is between 10° C. and 40° C., and
      (iii) initiates initial delivery of the drug by the drug delivery apparatus following expiration of the calculated time delay, regardless of the temperature of the temperature sensitive component following expiration of the calculated time delay.

18. The portable drug delivery apparatus of claim 17, wherein the processor receives from the temperature sensor the initial sensed temperature of the temperature sensitive component while the recipient is at a medical institution and initiates the initial delivery of the drug after the recipient leaves the medical institution.

19. The drug delivery apparatus of claim 17, wherein the predetermined working temperature is between room temperature and body temperature.

20. The drug delivery apparatus of claim 19, wherein body temperature is between 36° C. and 38° C.

* * * * *

UNITED STATES PATENT AND TRADEMARK OFFICE
CERTIFICATE OF CORRECTION

PATENT NO. : 10,335,545 B2
APPLICATION NO. : 14/372384
DATED : July 2, 2019
INVENTOR(S) : Oz Cabiri Page 1 of 1

It is certified that error appears in the above-identified patent and that said Letters Patent is hereby corrected as shown below:

In the Claims

Column 16, Line 51-Column 17, Line 7, (approx.), Claim 1 should be corrected as follows:
A drug delivery apparatus, comprising:
    a drug reservoir that stores a drug therein;
    a temperature sensitive component that is at least one of the drug, the drug reservoir, or a power source that powers the drug delivery apparatus;
    a temperature sensor in thermal communication with the temperature sensitive component to sense a temperature of the temperature sensitive component;
    a transcutaneous device;
    a pump coupled to the transcutaneous device to deliver the drug via the transcutaneous device; and
    a processor that:
    (i) receives from the temperature sensor an initial sensed temperature of the temperature sensitive component prior to initial delivery of the drug,
    (ii) calculates a time delay for the temperature sensitive component to reach, starting from the initial sensed temperature, a predetermined working temperature that is between 10° C. and 37° C., and
    (iii) initiates initial delivery of the drug by the drug delivery apparatus following expiration of the calculated time delay, regardless of the temperature of the temperature sensitive component following expiration of the calculated time delay.

Signed and Sealed this
Twentieth Day of October, 2020

Andrei Iancu
*Director of the United States Patent and Trademark Office*